United States Patent
Geissler et al.

(10) Patent No.: US 6,250,379 B1
(45) Date of Patent: Jun. 26, 2001

(54) HIGH-SPEED CAPILLARY TUBE HEAT EXCHANGER

(75) Inventors: Stefan Geissler, Dortmund; Karl Heinz Schweitzer, Unna; Helmut Beykirch, Menden; Gert Langer, Fröndenberg; Udo Werner, Recklinghausen, all of (DE)

(73) Assignee: hde Metallwerk GmbH, Menden (DE)

( * ) Notice: Subject to any disclaimer, the term of this patent is extended or adjusted under 35 U.S.C. 154(b) by 0 days.

(21) Appl. No.: 08/442,103

(22) Filed: May 16, 1995

(30) Foreign Application Priority Data

May 17, 1994 (DE) ................................. 44 17 266
Jan. 10, 1995 (DE) ............................... 195 00 421

(51) Int. Cl.⁷ ................................. F28D 7/02; F28F 9/22
(52) U.S. Cl. .......................... 165/158; 165/162; 165/163; 165/174; 165/145
(58) Field of Search ................................. 165/158, 173, 165/175, 174, 162, 163, 133

(56) References Cited

U.S. PATENT DOCUMENTS

| | | | |
|---|---|---|---|
| 2,181,486 | * 11/1939 | Jenkins | 165/162 X |
| 3,513,908 | * 5/1970 | Singh | 165/163 X |
| 4,924,938 | * 5/1990 | Plaschkes | 165/158 |
| 4,999,102 | * 3/1991 | Cox et al. | 137/561 A X |
| 5,058,663 | * 10/1991 | Hagemeister | 165/162 |
| 5,241,839 | * 9/1993 | Hughes | 165/174 X |
| 5,246,062 | * 9/1993 | Meijburg | 165/158 X |
| 5,301,746 | * 4/1994 | Trage et al. | 165/113 |

FOREIGN PATENT DOCUMENTS

| | | | | |
|---|---|---|---|---|
| 211796 | * | 4/1960 | (AU) | 165/174 |
| 28388 | * | 11/1917 | (NO) | 165/158 |

* cited by examiner

*Primary Examiner*—Leonard Leo
(74) *Attorney, Agent, or Firm*—James Creighton Wray; Meera P. Narasimhan

(57) ABSTRACT

For the sterilization of liquids (43) containing harmful microorganisms, or for the conditioning of mixtures of substances, a process and a heat exchanger (1) in the form of a tubular heat exchanger are used. The tube bundle (3) between the intake flange (2) and the outlet flange (4) is comprised of a number of tubes (18, 20) that are equal in length and that possess a narrow flow area and thin walls. These tubes, characterized as capillary tubes, are connected via distribution canals (15, 16) that are equal in length and similar in cross-section, to the central tube (12, 13) in the intake flange and in the outlet flange (2, 4). This causes the residence time distribution in the heat exchanger (1) to be held within very narrow limits, and causes the medium to be heated within fractions of a second to, for example, 140° C. or more, or less. This ensures a sterilization with the best possible preservation of thermolabile components, such as vitamins and proteins.

39 Claims, 3 Drawing Sheets

HIGH-SPEED CAPILLARY TUBE HEAT EXCHANGER

BACKGROUND OF THE INVENTION

The invention involves a heat exchanger for the thermal conditioning of mixtures of substances or for the sterilization of liquids that are or may be contaminated with microorganisms, having an intake flange and an outlet flange and a tube bundle that connects these two flanges, which is sealed inside a shell having ports for the feeding-in and removal of the heating medium. The invention also involves a process for the thermal conditioning of mixtures of substances or for the sterilization of liquids.

Heat exchangers of this type are used, for instance, in the food processing industry, the pharmaceutics industry, and in biotechnology fields, as well as in other areas of process engineering in which liquid media must be heated to high temperatures in the shortest time possible. This heating results in the sterilization of these liquids by killing off undesirable microorganisms and microbes. One problem, however, is that heat labile components and useful materials, such as vitamins and proteins, also become denatured in the process of heat treatment, with the duration of the heat treatment being of primary importance in terms of this negative effect. This so-called denaturation is a particular problem in what is termed the discontinuous sterilization process, which generally involves long heating-up, residence, and cooling times. An additional disadvantage to the process of discontinuous sterilization is that the packaging must also be heated for sterilization. For this reason, continuous sterilization, in which short residence times are possible, is preferred. In the food processing industry, the ultra-high temperature processing of milk is a particularly well-known example of this.

For this known process of continuous sterilization, parallel-plate heat exchangers are generally used in industry. These are comprised of plates that are layered one on top of another and contain special, waved indentations that form the flow canals. These plates are generally pressed together in large numbers by means of tension rods between thick-walled holding plates, and support one another, according to the shape of the waves, at several points. The distance between the plates ranges from 2.5 to 12 mm, which creates correspondingly varied flow canal sizes. The product of value and the heat-exchanging medium flow alternatingly between every two plates. Depending upon the design, the flow paths for the product of value in the individual canals, from the intake opening to the outlet opening, are of varying lengths in all design types, regardless of whether the overflow of the plates is diagonal or curved. This necessarily creates a correspondingly broad residence time distribution for the products to be sterilized using these known parallel-plate heat exchangers, with the result that a certain portion of the heat-sensitive components, for which the period spent in the heat exchanger lies above the average residence time, are subjected to severe denaturation. An even wider range of residence times is created by the hydraulic boundary layers or dead areas that are created at the points of contact of adjacent plates, in which the rate of flow naturally drops to very low levels.

In general technology, tubular heat exchangers are known; these advantageously contain large flow areas and flow paths that are equal in length. Liquids that flow through these tubes have an equal distribution of residence times. The disadvantage of these heat exchangers, however, is that due to the correspondingly varied feeding-in of the medium from the central feed tube, radically dissimilar flow paths and varied residence times are created. In addition, these known tubular heat exchangers are unsuitable for the sterilization of liquids or for the conditioning of mixtures of substances because they do not permit short-time sterilization within the range of seconds.

SUMMARY OF THE INVENTION

It is thus the object of the invention to create a heat exchanger and a sterilization process that are also suited for short-time sterilization and that ensure a uniform residence time and sterilization temperature.

The object is attained in accordance with the invention in that the tube bundle contains several tubes that are equal in length and similar in cross-section, and that are connected to the central tube via distribution canals, positioned in the area of the intake and/or outlet flange, that are also equal in length and similar in cross-section.

This design for a heat exchanger, in which the medium flows through several tubes that are equal in length and similar in cross-section, but remains evenly distributed among the tubes, ensures a residence time distribution that remains within very narrow limits. The medium, which is fed through the tubes having the corresponding flow area, can, for example, be heated to 140° C. within tenths of a second, thus the required sterilization with the most extensive possible preservation of the vitamins and proteins can be guaranteed. It is thus possible to use a type of tube-bundle heat exchanger even in the food processing industry and in related industries, as equal residence times and sterilization temperatures can be guaranteed with these heat exchangers.

In relation to this, it is particularly advantageous for the tubes to have a very narrow flow area and thin walls, as this will permit an even and rapid increase in temperature over a short distance for the medium in the tubes. The capillary tubes that are used, which are equal in length and have very narrow flow areas, also make it possible for prime foodstuffs or similar goods to be sterilized gently but within the necessary time and at the required temperature, without danger of damage to the liquid itself.

In accordance with one advantageous embodiment of the invention, the tubes are either circular or oval in their cross-section. Although the tubes may theoretically possess any cross-sectional shape, the specified circular or oval tubes can be easily and accurately combined to form the corresponding tube bundles, even with their narrow or thin walls that are specified in the invention. They may also, in accordance with the invention, be flat or rectangular in cross-section, with the advantage that this shape provides, depending upon the volume of the liquid, a greater heat exchange surface in the capillary tubes.

In order to effect the heating of the medium to, for example, 140° C. within the required short period of time, correspondingly short tubes having an inside diameter, or transverse length, of between 0.5 and 5 mm, preferably 1.0 to 3.0 mm, are used. As a result of their relatively small cross-section, these tubes provide a defined length and a defined flow which enables a precise control of or compliance with the desired temperature values. This is also true for the further embodiment of the invention, in which the tubes have a wall thickness of 0.05 to 1 mm, preferably 0.1 to 0.3 mm. With these, and with a precisely defined cross-section, an even heating of the medium within the shortest time possible can be ensured.

Even with the shortest possible flow rates (laminar flow range), the desired heating is ensured under optimum conditions, since, in accordance with a further advantageous embodiment of the invention, the tubes are designed to be positioned evenly over the cross-section of the shell and to be curved or coiled into a helix or a meandering shape. Regardless of the cross-section of these tubes that have been curved or coiled into a helix or a meandering shape, so-called secondary flows are superimposed upon the primary flow, crosswise to the axial flow, which causes the pulse exchange as well as the heat exchange to be increased significantly due to the increased convection. Because such forced changes in the direction of flow occur over and over along the entire length of the tube, the result is the above-mentioned significant improvement in or acceleration of the heat exchanger, as well as a limitation of the residence time distribution. It is also an advantage that this arrangement and design of the tubes enables a substantial reduction in the dimensions of the individual heat exchangers, down to the milliliter range.

It can also be advantageous in increasing the heat exchange for the inner and/or outer walls of the tubes to be profiled. These flow impediments on the inside walls or the outside walls will cause the hydraulic boundary layer to be disrupted by burbles (swirling), thus creating substantial improvement in the pulse exchange and heat exchange crosswise to the primary direction of flow.

As has already been indicated, with the invention it is ensured that equal amounts of the liquid medium are admitted via distribution canals into the individual tubes. This is achieved primarily in that the distribution canals are designed to be arranged in a stellate pattern around the central bore hole, which is connected to the central tube, and to feed into the tubes, which are arranged in a circular pattern, at equal distances from one another, around the central axis. If, for example, ten tubes are used, then ten uniformly designed distribution canals extend radially toward the outside from the central bore hole, ensuring that the individual tubes each receive equal amounts of the medium, from the very beginning, via the central tube. The distribution canals are uniformly designed and equal in length, so that, independent of the rate of flow, a short-time sterilization process, in which equal residence times are maintained, can be carried out.

If the feeding-in of the medium that is to be sterilized or conditioned varies, it can be advantageous for the distribution canals to be equipped with regulating devices that operate either individually or as a group to close individual distribution canals or entire groups of canals, thus causing the medium to be directed through the remaining distribution canals and tubes at an even rate of flow. The rate of flow can be varied by admitting the medium to different capillary tubes.

To facilitate the even feeding of the medium into the tubes, and to permit the inclusion of the appropriate regulating devices if necessary, the distribution canals are designed to be positioned in the intake flange or the outlet flange, with the corresponding end flange of the shell having a completely smooth surface. This also creates a metallic seal, which ensures the even feeding of the medium into the tubes via the distribution canals, without requiring additional measures.

In place of the above-mentioned regulating devices, a change in the number of distribution canals can be achieved by exchanging the intake flange or outlet flange that contains the distribution canals. This can be done easily, since in accordance with an advantageous embodiment of the invention the two end flanges are connected via support tubes which contain connecting bolts, and since the end flanges are connected to the intake or the outlet flange via separate securing screws. In this way, the intake or outlet flange can be separated from the corresponding end flange and replaced by another flange containing a different number of distribution canals, practically without affecting the remaining components of the heat exchanger. The two end flanges may advantageously be connected directly to the shell via soldering or welding.

The embodiment for the heat exchanger specified in the invention also enables either a modular parallel coupling of several heat exchangers of this type, or a series coupling, enabled by the fact that the intake and outlet flanges are designed to correspond with and be coupleable to the shells of other heat exchanger modules. As will be explained further on, this also provides the option of forming a complete unit comprised of several heat exchangers of this type, which are all similar in design and thereby possess similar capacity data. The series coupling of heat exchangers also carries with it the advantage that the residence time can be selectively increased, if this is necessary for some reason, by simply "affixing" a correspondingly proportioned and designed module to the heat exchanger. This residence module may also contain other suitable flow tubes, with "interfaces" that are structurally appropriate in design.

As the heating or cooling media, steam, gases, or liquids may be used, with the feeding-in tubes for these media being securely fastened to the shell via correspondingly tangentially arranged ports. This ensures an even distribution of the heating medium inside the shell.

In order to enable both counterflow and parallel flow operation, for example using heat exchanger oils, the device in the invention contains two ports for the heating medium, which are 180° from each other, at the intake and the outlet sides of the device. Each of these heating medium ports is positioned near the end flange on either the intake or the outlet side.

In order to prevent the mechanical deformation of the thin-walled tubes over the length of the shell, and to prevent them from shifting in relation to one another, the positioning of the tubes is stabilized by holding devices that are distributed at specific distances from one another over the entire length of the shell. These holding devices are designed and constructed such that they impede the flow of heat only minimally.

In the case of helix-shaped capillary tubes, the holding devices are designed as star-shaped support elements, but in the case of the meandering tube coil they are designed as spacing disks which ensure that the tubes are kept a specific distance from one another while at the same time stabilizing them. A similar type of holding device is designed for oval-shaped tubes.

In the case of a parallel coupling of several heat exchanger modules, it is advantageous for the modules to be connected parallel to one another in a stellate arrangement. This permits the quantity of the medium that is to be sterilized to be appropriately increased, without requiring additional, more costly designs. This arrangement also carries with it the advantage that individual heat exchanger modules that are part of the parallel coupling can be closed at no great expense, if the quantity that is to be fed through the device is to be reduced or must be reduced.

As was pointed out earlier, in addition to the parallel coupling, a series coupling of similarly constructed heat exchanger modules is also possible, in which, in accordance with the invention, three heat exchanger modules that are similar in construction are connected to one another to form a complete unit comprising a heating stage, a residence stage, and a cooling stage. The primary advantage of this is that it allows a complete sterilization to be performed, from normal temperature through heating and cooling and back to normal temperature, without requiring any additional intermediate piping of the medium that is to be sterilized. This ensures the even piping of the medium in each individual tube, over the entire length of the complete unit, with optimum effect for heating as well as for cooling, while maintaining a narrow and invariably even residence time distribution.

To simplify this complete unit, the invention further provides for the center residence stage to be directly connected to the heating and the cooling stages, without an intermediate connection to the intake or outlet flange, so that corresponding intake and outlet flanges are required only at the ends of the heating or cooling stage.

In order to prevent the product components from adhering to the walls of the tubes, the invention provides for the distribution canals and/or the tubes to have a coating on their inner wall surface, which is comprised of a hydrophobic or lyophobic material, preferably paraffin wax. In this way, agglomerations, which would necessarily lead to negative surface effects, but more importantly would inhibit the desired even heating of the liquid or the mixture of substances, are prevented.

It is also possible for the distribution canals and/or the tubes to be comprised entirely of a hydrophobic or lyophobic material, such as teflon, polypropylene, or a similar material.

An optimization of residence time can be achieved in accordance with the invention in that the distribution canals are equipped with connecting ports, which are connected to a vessel that 1 contains a separating fluid and is equipped with a distribution system. The distribution system causes a separating fluid to be fed into the liquid flow from the vessel at preset intervals, causing plugs to form, which separate the individual sub-quantities of liquid from one another. This separation of the individual liquid plugs prevents back-mixing and ensures the treatment of specific quantities of liquid on the way through the capillary tubes. This advantageous limitation of the residence time distribution is promoted by the fact that within each individual liquid plug a circulating flow is created, and the thorough mixing of the liquid that this causes within a plug also contributes to the further limitation of the residence time distribution.

This advantageous prevention of back-mixing and creation of a circulating flow are achieved primarily in that the vessel is designed as a tank for inert gases or steam, so that the plugs that are fed in intermittently are gas bubbles, comprised of either inert gas or steam.

In order to permit a wide range of possible variations, it is advantageous for the distribution system for all the distribution canals, for individual canals, or for groups of distribution canals to have a segmented liquid flow. For this purpose the distribution system contains valves that are operated separately, or similar control elements, which permit both the term and the quantity of the separating fluid being regulated to be altered or, if necessary, even obstructed.

For the conditioning of mixtures of substances or for the sterilization of liquids that are or may be contaminated with microorganisms, a process is used, in which the indirect heating of the mixtures of substances or liquids is performed via a very specific manner and means, in which the mixture of substances or the liquid flow is divided into precisely defined split streams containing approximately equal quantities, and each split stream is heated at the same speed for a preset period of time, after which, preferably following the rejoining of the split streams, the liquid flow is further treated. This process is effected using a heat exchanger, which is characterized in the preceding claims 1 through 27 or by individual features specified therein. The separation of the liquid flow into the smallest possible, and thereby, particularly in terms of the quantity, into the most precisely defined split streams, makes it possible to warm these many split streams evenly within the given unit of time, to heat them, to hold them for a preset period of time at this temperature, and, if necessary, to cool them off afterward. In addition, a residence time distribution is provided for that is limited to the point that will ensure the desired even and effective heating of the liquid flow or the flow of the mixture of substances.

In order to enable the further limitation of the residence time distribution, it can be advantageous to heat the split streams separately in modules that are connected to one another, to hold them at this temperature, and to cool them off, after which they can be rejoined. Particularly in terms of the cooling-off stage, such a separation into different module units can be advantageous, as then the necessary conditions created by a systematic cooling process can best be realized.

Agglomerations of individual product components or product mixtures are effectively prevented in that the distribution canals and/or the tubes are equipped with a coating on their inside walls, made of a material that eliminates surface effects, preferably paraffin wax or a similar compound. This coating, for example in the form of paraffin, leads to a maintenance of the flow of product or the liquid flow, without risk of adverse effects to the flow caused by an agglomeration on the inner wall.

In place of the coating on the inner wall, a design is possible in which the distribution canals and/or the tubes as a unit are made of a hydrophobic or lyophobic material such as teflon or polypropylene.

The calculated, successive feeding of a separating medium, via a suitable distribution system, into individual tubes, or even into all the tubes, results in a segmented liquid flow, so that the individual liquid segments pass through the system via the plug flow that is thus created, with the most clearly defined residence time. The process provides for a separating medium that will mix with the split streams [sic] to be fed into the split streams at preset intervals, with inert gas or steam bubbles being preferably used as the separating medium. The separating medium, preferably in the form of inert gas or steam bubbles, is funneled into one split stream, several split streams, or groups of split streams. The most precisely defined residence time created by the formation of plugs is based on the fact that the gas bubbles present between the liquid plugs prevent an axial back-mixing among several liquid plugs, which ensures a very narrow residence time distribution. This advantageous limitation of the residence time distribution is further promoted by the fact that a circulation flow is created within each individual liquid plug, and the thorough mixing of the liquid that this causes has a correspondingly positive effect.

The invention is distinguished specifically by the fact that a heat exchanger is created that can be used both for continuous short-time sterilization and for the conditioning of mixtures of substances via heat treatment, with the optimal, most extensive preservation of heat-sensitive products of value, in which a constant supply of heat, very short residence times, and a narrow residence time distribution are maintained. The medium flows through tubes that are equal in length, which in this case are characterized as capillary tubes due to their narrow flow area, in which, prior to intake of the medium into the capillary tubes, from the central tube, via distribution canals that are equal in length and similar in design, a preliminary and specifically defined partition of the medium into the capillary tubes occurs. As a result of this partition, the residence time distribution is held within very narrow limits. The capillary tubes themselves may have any cross-sectional shape, however tubes that are circular or oval in their cross-section are advantageously used. For the generation of heat, any medium such as steam, liquids, electrical heating sources, etc. may be used; the same is true for the cooling medium. The specific design of the capillary tubes ensures an optimal heat exchange, which can be improved upon via counterflow operation, flow spoilers, or cross-current flow operation. Above all, however, the capillary tubes can be relative simply used, which causes the shell, with its individual components and its seals, to be widely applicable. Alternatively, the invention provides for a version in which the capillary tube bundle and the end flanges are directly welded or soldered to the shell. Advantages to this design include extremely rapid heating and cooling, particularly in the case of embodiments that are curved or coiled into a helix or a meandering shape. Reference has already been made to the narrow residence time distribution. A further advantage that should be mentioned, however, is that there is hardly any risk of blockage in the case of capillary tubes that are round or rectangular in cross-section, since they contain no flow baffles. With the use of appropriate materials, such as special steel for example, the sterilization of the entire heat exchanger device is facilitated, with the absence of the flow baffles also enabling a more thorough cleaning. The invariably even cross-sections, quantities, and flow make a simple and specifically defined scale transference possible, in other words, with the same structural design, any number of similar modules may be connected in order to achieve greater throughrates. The liquids pass through all of the tubes under the same conditions. With a calculated feeding-in of inert gas or steam bubbles via the distribution system, the most specifically defined residence time for the individual liquid plugs or for the liquid streams is ensured. Disadvantageous surface effects are prevented by either coating the tubes or distribution canals with a hydrophobic or a lyophobic material, or making the tubes or distribution canals entirely of such a material.

Further details and advantages of the object specified in the invention are given in the following description of the attached diagrams, in which preferred exemplary embodiments containing key details and individual components are illustrated. These show:

DETAILED DESCRIPTION OF THE PREFERRED EMBODIMENTS

Figure 1:
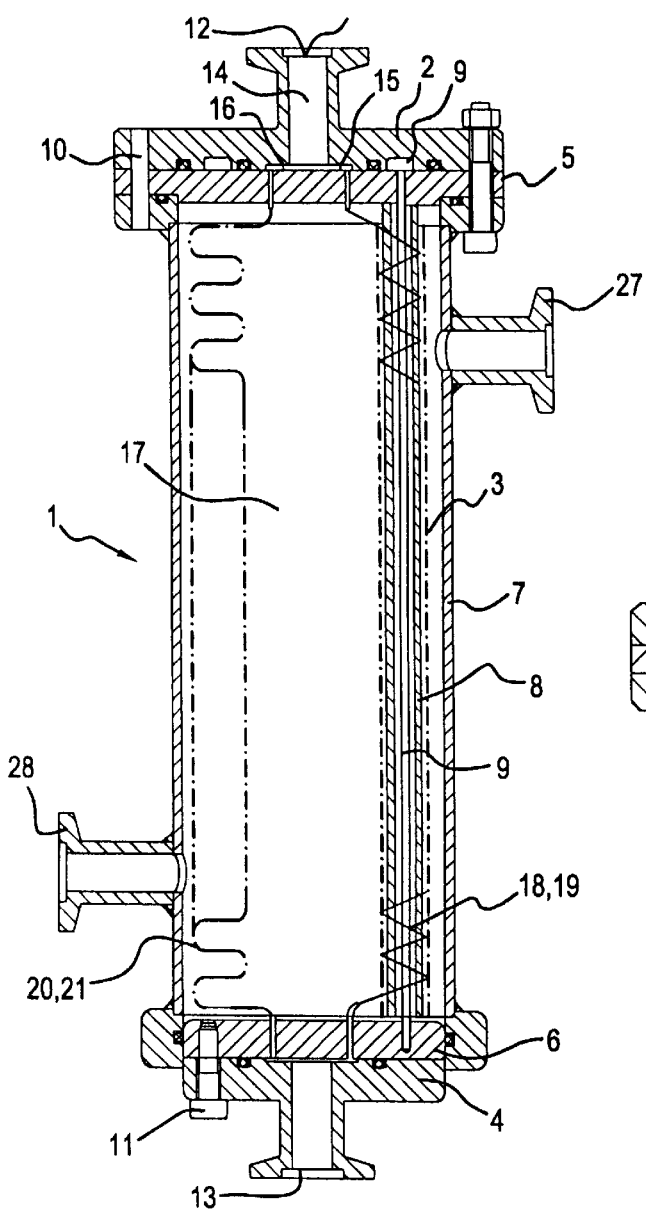
FIG. 1 a longitudinal cross-section of a heat exchanger having tubes that are curved into a helix or meandering shape, FIG. 2 and FIG. 3 a partial longitudinal cross-section and a partial cross-section of a heat exchanger having tubes that are oval in shape, FIG. 4 a cross-section of a heat exchanger in which the tubes are stabilized via holding devices, FIG. 5 an overhead view of the end flange side of an intake flange, FIG. 6 a complete unit, comprised of a number of heat exchangers, FIG. 7 an oval tube with profiling, FIG. 8 a magnified representation of the tube with profiling, FIG. 9 a cross-section of the tube in accordance with FIG. 7 and FIG. 8, FIG. 10 a longitudinal section of a tube containing plugs that have been formed via feeding-in of a separating medium, FIG. 11 a cross-section of a tube having a coating on its inner wall, FIG. 12 a longitudinal section of a tube containing distribution system ports, FIG. 13 the upper section of a heat exchanger containing a distribution system, and FIG. 14 an overhead view of the intake or end flange, with components of the distribution system.

FIG. 1 illustrates a basic design of a heat exchanger 1 in accordance with the invention, in which two variations on the design of the tube bundle 3 between the intake flange 2 and the outlet flange 4 are given. The tube bundle 3 is bordered at both ends by end flanges 5, 6, and is enclosed at its sides by a shell 7. Each individual component of the tube bundle 3 is equipped with a support tube 8 that contains a connecting bolt 9, so that a tightening of the connecting bolt 9 will cause the two end flanges 5, 6 to be braced firmly against one another, and against the support tube 8 and the entire tube bundle 3.

In addition, the end flanges 5, 6 are separately connected to the intake flange 2 or the outlet flange 4 via securing screws 10, 11, so that the intake flange 2 and the outlet flange 4 can be individually separated from the corresponding end flanges 5, 6.

The liquid or the medium that is to be treated is fed into the heat exchanger 1 via the upper central tube 12 and the central bore hole 14, and is divided evenly from the very beginning among the individual tubes 18, 20 of the tube bundle 3. The helix-shaped tube 19, or the meandering tube coil 21 are arranged evenly around the center axis 17, so that all of the tubes 18, 20, which extend in a stellate pattern, as will be specified in greater detail at a later point, can simultaneously receive the medium via the distribution canals 15, 16.

The medium is then removed from the tubes 18, 20 at the lower end, via the end flange with its associated bore holes and holding devices, and is fed back to the central tube 13 via the distribution canals that are also positioned in the lower end, after which it is discharged from the heat exchanger.

Figure 3:
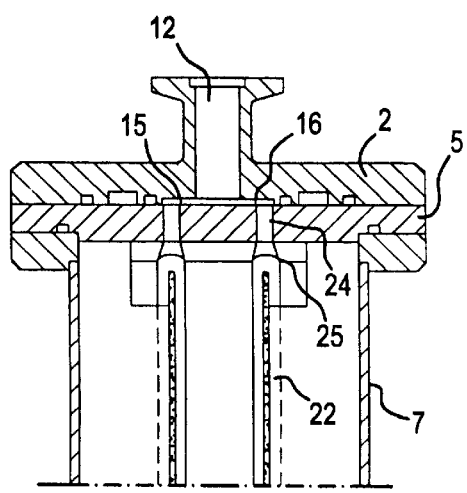
Figure 2:
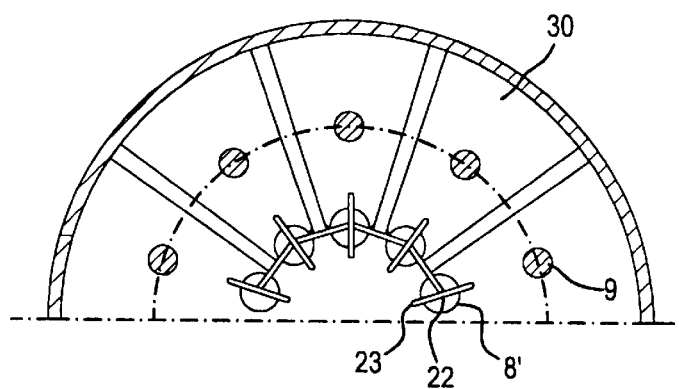

Rather than the embodiment of the tubes 18, 20 illustrated in FIG. 1, which are in the form of a helix 19 or a meandering tube coil 21, an application is also possible in which the tubes 22 are oval in shape, as illustrated in FIG. 2 and FIG. 3; these tubes may be used with or without profiling sections 23. The upper part of FIG. 3 shows a magnified representation of the upper flanges 2 and 5, with the corresponding distribution canals 15 and 16. The profiling section 23 may be positioned on the inner wall 24 or on the outer wall 25, or even on both walls.

For the heating or cooling media, steam, gases, or liquids, such as heat exchanging oil or other liquid media, may be used. This heating medium is fed into the shell 7 via the heating medium port 27, which is positioned near the flange 2, 5, and is removed via the heating medium port 28 at the lower flange 4, 6. These heating medium ports 27, 28 on the shell side of the heat exchanger 1 are preferably tangentially arranged, in order to ensure an even distribution of the heating medium. Each two ports are displaced 180° and are positioned near the end flanges 5 and 6, in order to enable both counterflow and parallel flow operation.

Figure 4:
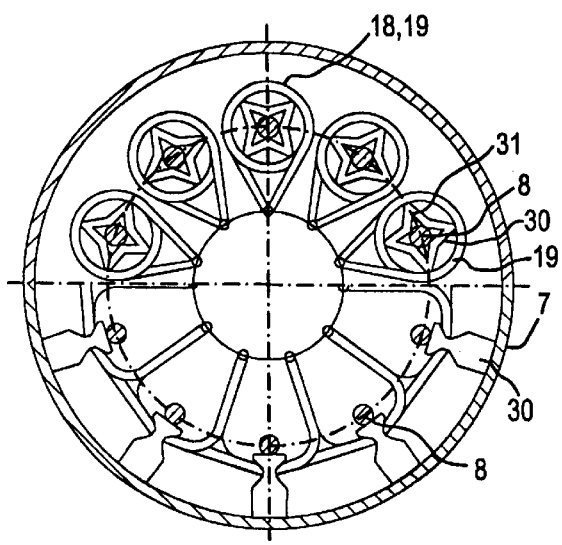

In order to prevent a mechanical deformation of the tubes 18, 20 or a shifting of the tubes in relation to one another, the tube bundles or the tube bundle 3 are equipped with holding devices 30, positioned at appropriate distances from one another. Various embodiments for these holding devices 30 are possible, as is indicated in FIG. 2 and 4. In the case of the helix-shaped tube 19, the tubes 18, 20 are coiled around star-shaped support elements 31, as illustrated in FIG. 4. The tube bundle with the meandering, curved tubes 18, 20 is spaced and mechanically stabilized via several spacing disks 32 that are distributed evenly over the length of the tube, as is illustrated in FIG. 2. A similar holding device 30 is provided for the oval tubes 22.

Figure 5:
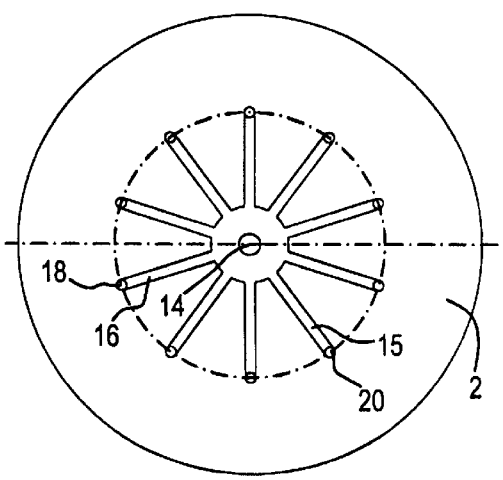

FIG. 5 shows an overhead view of side of the intake flange 2 or the outlet flange 4 that is closest to the end flange 5 or 6. More precisely, this is the outlet flange 4, since the recesses that would contain the heads of the connecting bolts 9, or a corresponding channeled nut, are not present in the flange illustrated in FIG. 5. It can be clearly seen, however, that the outlet flange 4 contains distribution canals 15, 16 that extend from the center bore hole 14 in a star-shaped pattern, and that extend to the tubes 19 [sic], 20 or to the bore holes that lead to these canals; the same is true for the intake flange 4.

In the embodiment illustrated in FIG. 5, ten such distribution canals 15, 16, corresponding to the number of bore holes 18, 20, are shown. When fewer bore holes 18, 20 of this type are present, the number of distribution canals is also reduced, or when some of the distribution canals are to be closed, then an outlet flange 4 or intake flange 23 that contains fewer distribution canals 15, 16 is used.

As has already been noted, it is a primary advantage of this heat exchanger design that quasi-optionally large heat exchanging surfaces for the treatment of correspondingly large volume fluxes can be realized with the modular parallel coupling of heat exchangers having distribution canals 15, 16 that are equal in length. This also ensures that the same flow and heat exchange conditions prevail in all of the tubes 18, 20, which results in an invariably narrow residence time distribution. The design of this heat exchanger enables development of the size of the required apparatus, and the necessary heat exchanging surface, without difficulty and with the guarantee of superior safety and precision.

Figure 6:
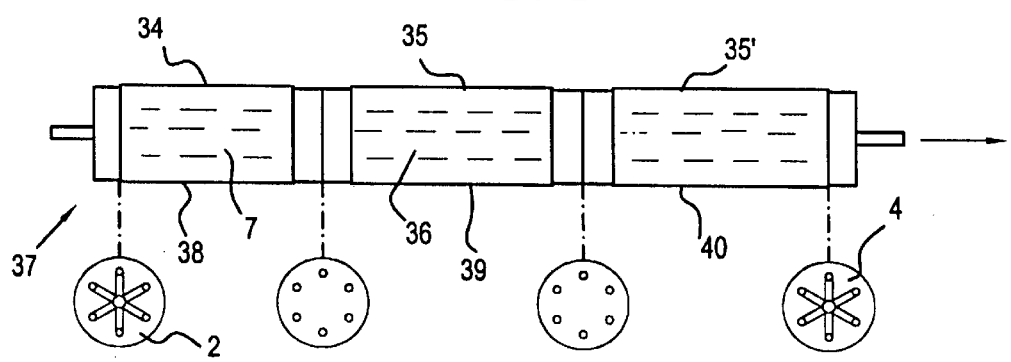

With the proposed heat exchanger design, both the heating-up, which occurs over a short period of time and proceeds with precise residence times, and the cooling-off of liquid media can be performed advantageously. In FIG. 6 a number of heat exchanger modules 34, 35, 35' are connected in series, to allow treatment of the liquid medium in this advantageous form. This design permits the entire unit 37 to be housed in one common shell 36, or alternatively in correspondingly connected partial shells. This advantageous form makes it possible to first heat the liquid media in the heating stage 38, then to hold the liquid for a specific period of time at a specific temperature in the residence stage 39, and finally to cool the liquid media to a specific temperature in a third stage, the cooling stage 40. This arrangement will permit any liquid, such as in the fermentation process in laboratory and technical units, to be sterilized in very small volumes and with very small volumetric flow rates, for example of approximately 0.1 to 10 l/h, based upon need. This object can be advantageously attained using the complete unit 37 that is illustrated in FIG. 6, in other words in the form of a continuous-operation, compact, high-speed capillary tube heat exchanger.

In the embodiment illustrated in FIG. 6, there is no indication, between the heating stage 38 and the residence stage 39, nor between the residence stage 39 and the cooling stage 40, of the positioning of intake flange 2 and outlet flange 4. These are included in this embodiment only the end area of the heating stage 38 or the cooling stage 40. In the areas in-between there is a direct transference from tube to tube. The corresponding cross-sections illustrated below FIG. 6 clarify this.

Figure 7:
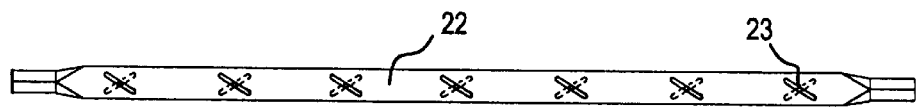
Figure 8:
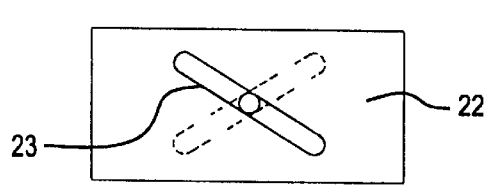
Figure 9:
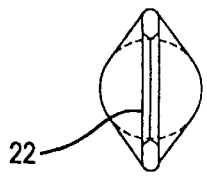

FIG. 7 shows a side-view of an oval tube 22, with a corresponding profiling section 23. One section of this is magnified and re-illustrated in FIG. 8, and FIG. 9 shows a cross-section with the corresponding oval tube 22 created from a round tube.

Figure 10:
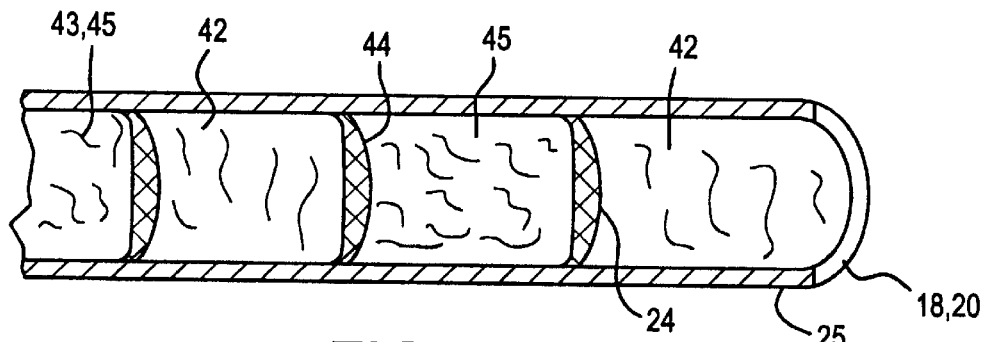

FIG. 10 shows a longitudinal section of a tube 18 or 20, which illustrates that a separating medium 42 is fed into the liquid 43, at specific intervals, so that individual liquid plugs are formed between the separating layers 44; these plugs can be particularly advantageously warmed or heated. In addition, the separating medium 42 can be fed in at very precisely timed intervals, allowing the creation of liquid plugs 45 that are equal in size.

Figure 11:
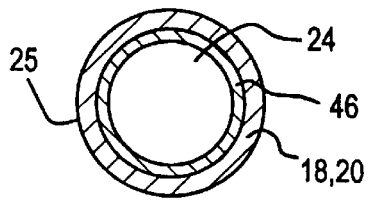

FIG. 11 shows a cross-section of a corresponding tube 18, 20, which contains a coating 46 on its inner wall in order to prevent surface effects caused by the agglomeration of product components, etc. This inner wall coating 46 is comprised in this case of paraffin wax that is evenly applied around the entire inner surface of the tube. It is also an option for the entire tube 18 or 20 to be comprised of a hydrophobic or lyophobic material, such as teflon or polypropylene, in order to prevent the above-described negative effects.

Figure 12:
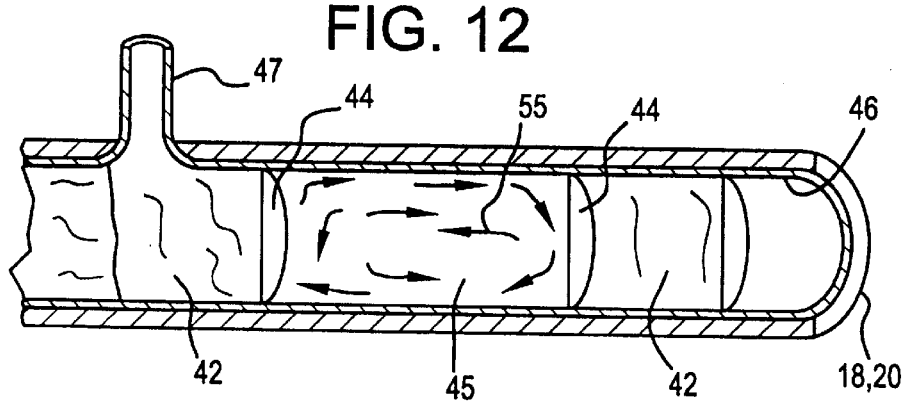

FIG. 12 is an expansion upon the illustration in FIG. 10, with the longitudinal section that is shown containing a corresponding coating on the inner wall 46. In addition, a connecting port 47 is shown, which is connected to the distribution system 50 or the tube system 49, neither of which is illustrated in this diagram. Inert gas or steam bubbles are fed in through these connecting ports 47, at preset intervals, creating the above-described plugs made of separating medium 42 or of inert bubbles.

It is further illustrated in FIG. 1 [sic] that within the individual liquid plugs 45 that are formed in this manner, an intermediate flow is generated, which contributes to an advantageous thorough mixing of the liquid, and thereby to the even affection and heating of this individual liquid plug. FIG. 2 [sic] also illustrates that the dimensions of the liquid plugs 45 and the gas bubbles or the bubbles of separating medium 42 need not be the same, rather that these may be extensively changed based upon prevailing conditions.

Figure 13:
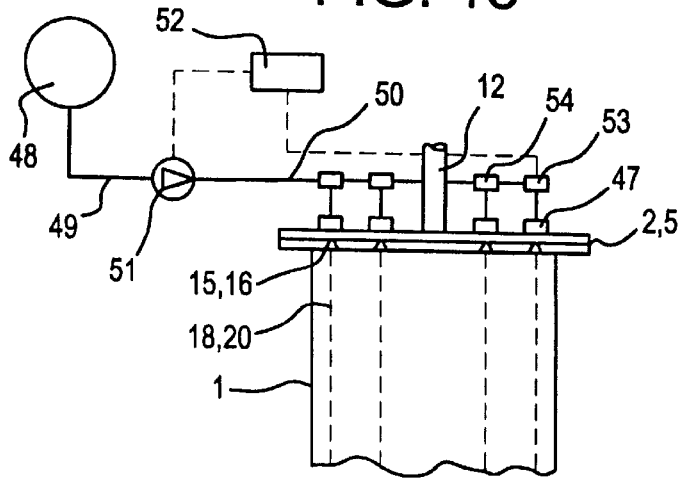
Figure 14:
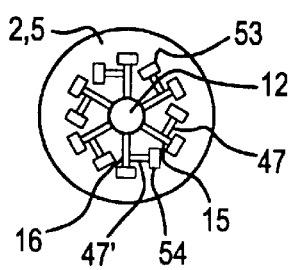

FIGS. 13 and 14 show a heat exchanger 1 that is equipped with a distribution system 50, on the side of the intake flange 2 and/or also the side of the outlet flange 4. This distribution system 50 ensures that optimal inert gas bubbles or bubbles of separating medium 42 are channeled into the liquid 43 or into the liquid flow, in order to encourage the plug formation as illustrated in FIG. 10 and FIG. 12. The gas required for this is held in the vessel 48 and is fed in through the tube system 49 of the appropriate connecting port 47. In the area of the distribution system 50, or within this system, a pump 51 is arranged, which operates in conjunction with the control component 52 and ensures that equal quantities of inert gas or steam flow into the system through the intermediate valves 53, 54, or that corresponding quantities of inert gas or steam flow into the system at the preset time intervals, in order to achieve the formation of plugs as illustrated in FIG. 10 and FIG. 12.

By means of the control component 52 and the intermediate valves 53, 54 that are assigned to the individual connecting ports, it is possible to connect individual tubes, all of the tubes, or even groups of tubes 18, 20 or distribution canals 15, 16 to the distribution system 50, in order to generate the appropriate bubbles of separating medium 42.

All characteristics, including those that are found only in the diagrams, are viewed alone and in combination as being vital to the invention.

What is claimed is:

1. A heat exchanger comprising an intake flange, an outlet flange, at least one bundle of plural tubes connecting the intake and the outlet flanges, a shell for encasing the at least one bundle between the flanges, an inlet port for feeding a heating medium into the shell, an outlet port for removing the heating medium, the plural tubes of the at least one bundle being of equal length and of similar cross-section, a central tube provided in the intake and/or the outlet flange, plural distribution canals connected to the central tube and to the at least one bundle of tubes, the distribution canals being of equal length and of similar cross-section as the plural tubes.

2. The heat exchanger of claim 1, wherein each of the plural tubes have a narrow flow area and thin walls.

3. The heat exchanger of claim 1, wherein each of the plural tubes have a circular cross-section.

4. The heat exchanger of claim 1, wherein each of the plural tubes have an oval cross-section.

5. The heat exchanger of claim 1, wherein each of the plural tubes have a rectangular cross-section.

6. The heat exchanger of claim 1, wherein each of the plural tubes have an inside diameter of 0.5 to 5 mm.

7. The heat exchanger of claim 6, wherein each of the plural tubes have an inside diameter 1.0 to 3.0 mm.

8. The heat exchanger of claim 1, wherein each of the plural tubes have a wall thickness of 0.05 to 1 mm.

9. The heat exchanger of claim 8, wherein each of the plural tubes have a wall thickness of 0.1 to 0.3 mm.

10. The heat exchanger of claim 1, wherein the plural tubes are evenly distributed over the cross-section of the shell.

11. The heat exchanger of claim 1, wherein the plural tubes are curved along the length of the shell.

12. The heat exchanger of claim 1, wherein the plural tubes are coiled along the length of the shell.

13. The heat exchanger of claim 1, wherein the plural tubes are helical the length of the shell.

14. The heat exchanger of claim 1, wherein the plural tubes have a meandering shape along the length of the shell.

15. The heat exchanger of claim 1, wherein the plural tubes have profiled inner and/or outer walls.

16. The heat exchanger of claim 1, further comprising s central bore-hole connected to the central tube, the distribution canals connecting the central bore-hole to the plural tubes, and wherein the plural tubes are equidistant from one another and form a circular pattern around a central axis of the shell, and wherein the plural tubes are arranged in a stellate formation in relation to the central bore-hole.

17. The heat exchanger of claim 1, further comprising at least one regulating element connected to the distribution canals for varying a rate of flow a substance from the distribution canals to the plural tubes.

18. The heat exchanger of claim 1, wherein the distribution canals are positioned in the intake flange or the outlet flange.

19. The heat exchanger of claim 18, wherein the end flange having the distribution canals has a smooth surface.

20. The heat exchanger of claim 1, further comprising plural support tubes having connecting bolts for connecting the intake and outlet flanges, and plural fasteners for connecting the intake and/or the outlet flanges on the shell.

21. The heat exchanger of claim 1, wherein the intake and outlet flanges are connected to the shell by solder or weld.

22. The heat exchanger of claim 1, wherein the intake and outlet flanges further comprise means for coupling with shells of adjacent heat exchanger modules.

23. The heat exchanger of claim 1, wherein the inlet and outlet ports are provided on sides of the shell in a tangential relation to each other.

24. The heat exchanger of claim 1, wherein the intake and outlet ports are provided proximal the intake and the outlet flanges, and are displaced by 180°.

25. The heat exchanger of claim 1, further comprising plural holders provided in the shell for holding and positioning the plural tubes in the shell.

26. The heat exchanger of claim 25, wherein the plural tubes are helix-shaped and wherein the holders are star-shaped.

27. The heat exchanger of claim 25, wherein the plural tubes are formed as a meandering tube coil and wherein the holders are spacing disks.

28. The heat exchanger of claim 1, further comprising plural heat exchanger modules connected parallel to one another.

29. The heat exchanger of claim 1, further comprising at least three heat exchanger modules connected to one another forming a complete unit comprising a heating stage, a residence stage, and a cooling stage.

30. The heat exchanger of claim 29, wherein the residence stage is directly connected to the heating and the cooling stages without intermediate connection to the intake and outlet flanges.

31. The heat exchanger of claim 1, further comprising a hydrophobic or lyophobic coating on inner walls of the distribution canals.

32. The heat exchanger of claim 1, further comprising a hydrophobic or lyophobic coating on inner walls of the tubes.

33. The heat exchanger of claim 1, wherein the distribution canals are of hydrophobic or lyophobic material.

34. The heat exchanger of claim 1, wherein the plural tubes are of hydrophobic or lyophobic material.

35. The heat exchanger of claim 1, further comprising connection ports connected to the distribution canals, a container having a medium for separation connected to the connection ports, and a distribution system connected to the container for distributing the medium to the distribution canals.

36. The heat exchanger of claim 35, wherein the container is a tank having inert gas.

37. The heat exchanger of claim 35, wherein the container is a tank having steam.

38. The heat exchanger of claim 35, wherein a segmented liquid flow is selectively delivered to all or some of the distribution canals by the distribution system.

39. The heat exchanger of claim 35, wherein a segmented liquid flow is selectively delivered to all or some of the plural tubes by the distribution system.

* * * * *